US012635886B2

(12) United States Patent
Ronda et al.

(10) Patent No.: US 12,635,886 B2
(45) Date of Patent: May 26, 2026

(54) ORAL ANALYSIS DEVICE

(71) Applicant: KONINKLIJKE PHILIPS N.V., Eindhoven (NL)

(72) Inventors: Cornelis Reinder Ronda, Aachen (DE); Martin Pekar, Eindhoven (NL); Jindrich Charvat, Statenice (CZ); Bernardus Hendrikus Wilhelmus Hendriks, Eindhoven (NL); Cristian Nicolae Presura, Veldhoven (NL); Amir Hussein Rmaile, Eindhoven (NL); Sandra Hotzl, Eindhoven (NL); Igor Wilhelmus Franciscus Paulussen, Nuenen (NL); Matthias Born, Eindhoven (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/873,025

(22) PCT Filed: May 16, 2023

(86) PCT No.: PCT/EP2023/063083
§ 371 (c)(1),
(2) Date: Dec. 9, 2024

(87) PCT Pub. No.: WO2023/237302
PCT Pub. Date: Dec. 14, 2023

(65) Prior Publication Data
US 2025/0352068 A1     Nov. 20, 2025

(30) Foreign Application Priority Data

Jun. 9, 2022     (EP) ..................................... 22178123

(51) Int. Cl.
A61B 5/00     (2006.01)
A46B 15/00     (2006.01)
A61B 1/24     (2006.01)

(52) U.S. Cl.
CPC ........ *A61B 5/0088* (2013.01); *A46B 15/0004* (2013.01); *A46B 15/0036* (2013.01);
(Continued)

(58) Field of Classification Search
CPC ....... A61B 5/0088; A61B 1/24; A61B 5/0002; A61B 5/0075; A61B 5/4547;
(Continued)

(56) References Cited

U.S. PATENT DOCUMENTS 4,479,499 A     10/1984     Alfano
6,024,562 A     2/2000     Hibst et al.
(Continued)

FOREIGN PATENT DOCUMENTS

WO     2014097045 A1     6/2014
WO     2014105521 A1     7/2014

OTHER PUBLICATIONS

International Search Report and Written Opinion Dated Aug. 31, 2023 For International Application No. PCT/EP2023/063083 Filed May 16, 2023.
(Continued)

*Primary Examiner* — Baisakhi Roy

(57)     ABSTRACT

A device and method for providing a classification of tooth surface materials using measured reflectance values for light within a particular optical band. In particular, at least two optical reflectance measurements may obtained within an optical wavelength band of 550 nm to 650 nm, and wherein a characteristic value proportional to a difference or ratio of those measurements is computed. This provides an indication, direct or indirect, of a sign of a slope of a reflectance (Continued)

spectrum within that band, and this has been identified through experiment as a reliable differentiator of healthy vs unhealthy enamel (presence of caries vs absence of caries).

15 Claims, 3 Drawing Sheets

(52) U.S. Cl.
CPC .............. *A61B 1/24* (2013.01); *A61B 5/0002* (2013.01); *A61B 5/0075* (2013.01); *A61B 5/4547* (2013.01); *A61B 5/6887* (2013.01); *A46B 2200/1066* (2013.01)

(58) Field of Classification Search
CPC .............. A61B 5/6887; A46B 15/0004; A46B 15/0036; A46B 2200/1066
See application file for complete search history.

(56) References Cited

U.S. PATENT DOCUMENTS

| | | | |
|---|---|---|---|
| 6,111,650 A * | 8/2000 | Rawicz | G01J 3/463 |
| | | | 356/402 |
| 8,345,924 B2 | 1/2013 | Wang et al. | |
| 2003/0156788 A1 | 8/2003 | Henning | |
| 2005/0181333 A1 | 8/2005 | Karazivan et al. | |
| 2007/0121786 A1 * | 5/2007 | Okawa | A61B 1/0615 |
| | | | 378/65 |
| 2009/0079993 A1 * | 3/2009 | Yatagai | A61B 5/7257 |
| | | | 356/497 |
| 2011/0102566 A1 | 5/2011 | Zakian et al. | |
| 2012/0104278 A1 * | 5/2012 | Downing | G01N 21/6428 |
| | | | 250/200 |
| 2016/0270716 A1 * | 9/2016 | Guan | A61B 1/000094 |
| 2018/0035896 A1 * | 2/2018 | Nozaki | A46B 15/0036 |
| 2020/0000215 A1 | 1/2020 | Jeanne et al. | |
| 2020/0138297 A1 | 5/2020 | Spruit et al. | |
| 2021/0059395 A1 * | 3/2021 | Kooijman | A46B 15/0004 |
| 2021/0141123 A1 * | 5/2021 | Sugawara | G02B 5/02 |
| 2023/0000604 A1 * | 1/2023 | Wang | A61C 19/066 |

OTHER PUBLICATIONS

Charvat, Jindrich et al. "Diffuse reflectance spectroscopy in dental caries detection and classification." Signal, Image and Video Processing / Revised: Jan. 8, 2020 / Accepted: Jan. 10, 2020 © Springer-Verlag London Ltd., part of Springer Nature 2020.

* cited by examiner

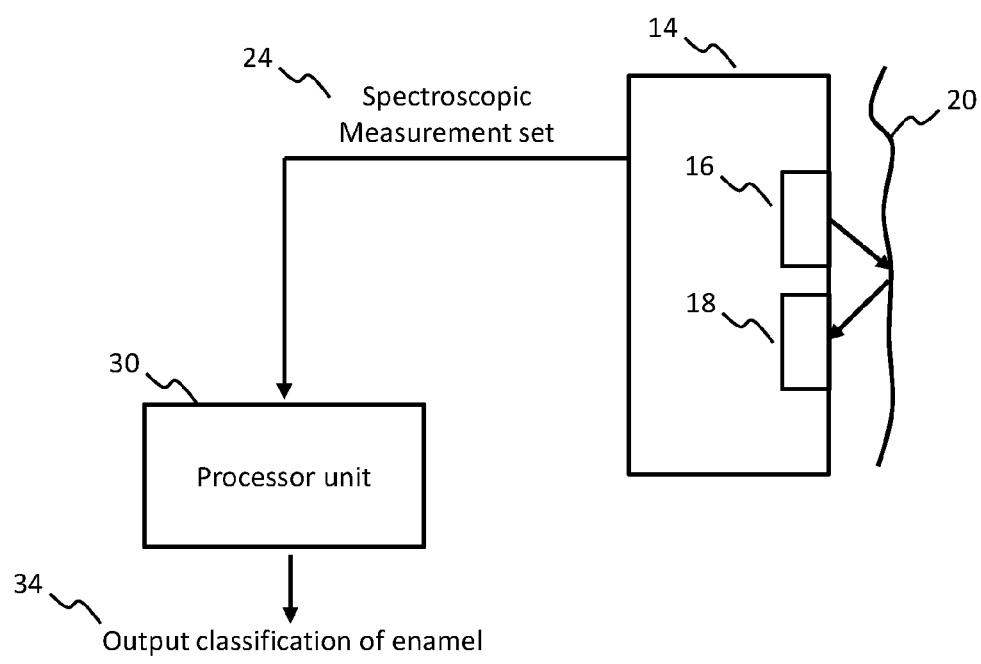

24
Spectroscopic
Measurement set

14

16

18

20

30

Processor unit

34
Output classification of enamel

FIG. 1

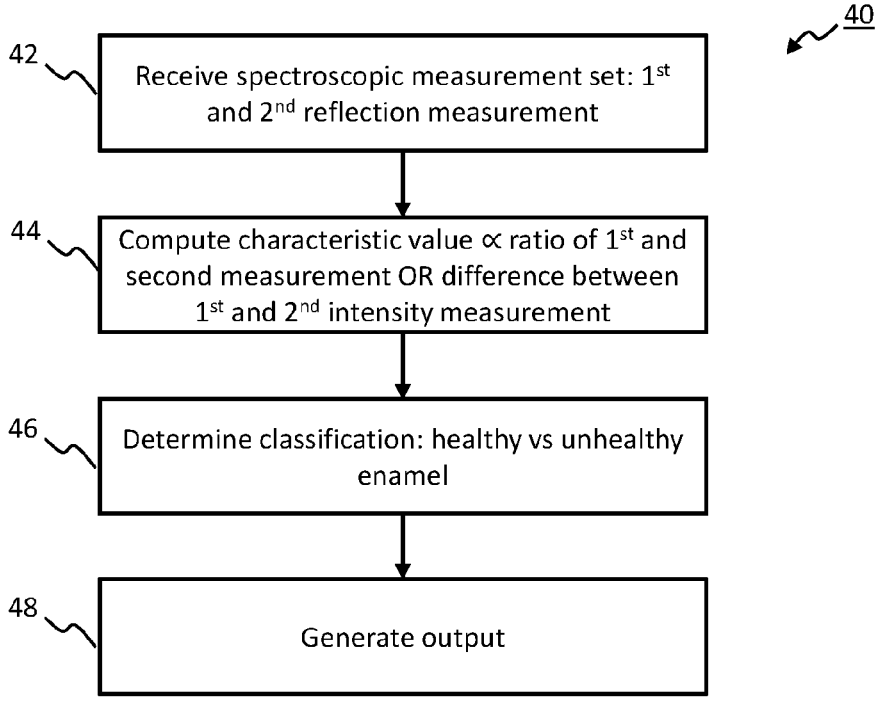

40

42
Receive spectroscopic measurement set: 1$^{st}$ and 2$^{nd}$ reflection measurement 44
Compute characteristic value ∝ ratio of 1$^{st}$ and second measurement OR difference between 1$^{st}$ and 2$^{nd}$ intensity measurement 46
Determine classification: healthy vs unhealthy enamel 48
Generate output

FIG. 2

ORAL ANALYSIS DEVICE

This application is the U.S. National Phase application under 35 U.S.C. § 371 of International Application No. PCT/EP2023/063083, filed on May 16, 2023, which claims the benefit of EP Application Serial No. 22178123.0, filed Jun. 9, 2022. These applications are hereby incorporated by reference herein.

FIELD OF THE INVENTION

The present invention relates to a device for oral analysis, particularly dental analysis.

BACKGROUND OF THE INVENTION

Examination of the oral cavity may be performed for various purposes, including for the detection of caries.

Caries is a well-known disease, which is encountered in more than half of the adult population. Especially when detected at an early stage, it is still reversible. For this reason, there is a clinical need for detecting caries in a person, so that if this is found to be the case, the person can be advised on improved oral hygiene routines or undergo treatment by a dental practitioner.

Oral examination for caries is most typically carried out through manual inspection by a dental practitioner.

It would be of advantage to provide a system capable of at least partially automating the process of inspection for dental caries.

SUMMARY OF THE INVENTION

The invention is defined by the claims.

An aspect of the invention is a dental analysis device. The dental analysis device comprises: a multi-frequency optical measurement apparatus comprising a light generator and a light detector, the light generator for irradiating a tooth surface with light during use, and the light detector for detecting a reflection of the light from the tooth surface during use. The light generator may be operable to selectively generate a light output within each of a plurality of different wavelength bands. Additionally or alternatively the light detector is operable to differentially detect light at each of a plurality of wavelength bands. The dental analysis device further comprises a processor unit comprising one or more processors. The processor unit is adapted to control the optical measurement apparatus to acquire a spectroscopic measurement set comprising at least two reflection intensity measurements at two different and non-overlapping wavelength sub-bands, each sub-band within the range 550 and 650 nm.

The processor unit is further adapted to compute a characteristic value from the at least two reflection intensity measurements, wherein the characteristic value is proportional to either a difference between the at least two reflection intensity measurements, or a ratio of the at least two reflection intensity measurements, whereby the characteristic value in either case provides a direct or indirect indicator of a sign of a slope of a reflection spectrum of the sampled surface between the respective wavelengths of the at least two measurements.

The processor unit is further adapted to determine a classification of healthy enamel vs unhealthy enamel based on the characteristic value.

The processor unit is further adapted to generate an output from the processor unit indicative of the classification. This may be a data output, a signal output, and/or a user-perceptible output for example.

The provided device is based on the concept of applying spectroscopic analysis to dental surfaces to classify a status of enamel for thereby determining (either automatically or by a dental practitioner) presence or absence of caries, or any other oral pathology. More specifically, it is proposed to use a diffuse reflectance spectroscopy technique in which diffuse reflected light is detected and analyzed. This contrasts for example with techniques using detection of florescence of surfaces responsive to optical illumination, and also with techniques which rely on use of coherent light. Use of diffuse light reflectance relaxes technical requirements for both the light generator and detector, meaning that for example a standard LED-based light generator can be used, and/or a simple set of one or more photodiodes or a camera chip can be used as the light detector.

The reader will note furthermore that the classification is derived in dependence upon a relative relationship between a plurality of reflectance intensity measurements, and does not depend on measurement of absolute reflectance intensity measurements, but only on relative intensity measurements. This also greatly relaxes the technical constraints on the detector used.

As will be explained with greater clarity later in this document, with reference to illustrative figures, the principle of the invention relies on a realization made by the inventors that, when the reflectance intensity spectrum is measured across the range approximately spanning from 550 nm wavelength to 650 nm wavelength, healthy enamel (that is, enamel without caries) very reliably shows a reflectance spectrum curve which has a negative gradient, while unhealthy enamel (that is, enamel with caries), very reliably shows a reflectance spectrum curve which has a positive gradient. It is this discovery that has led the inventors to further realize that this allows for classification of enamel as healthy vs unhealthy based on a relative relation between (at minimum) two reflectance intensity measurements at different points across this indicative range of the reflectance intensity spectrum. This can be a difference between a first and second measurement, or a ratio between the first and second measurement. Either will yield an indicator of whether the sign of the reflectance spectrum curve across the relevant range 550-650 is negative or positive, and from this a classification of the enamel derived.

It has been found that caries can be detected optically in the above-outlined manner at a relatively early stage, before irreversible cavities are formed, therefore enabling early treatment of the disease.

In some embodiments, the characteristic value is proportional to a ratio of the reflection intensity measurement of the lower of the at least two measured wavelengths to the intensity measurement of the higher of the at least two measured wavelengths. In this case, the processor unit determines a classification of healthy enamel responsive to the characteristic value being greater than or equal to 1 and determines a classification of unhealthy enamel responsive to the characteristic value being less than 1.

In a further set of embodiments, the characteristic value is proportional to a value of the intensity measurement for the higher of the at least two measured wavelengths subtracted from the intensity measurement for the lower of the at least two measured wavelengths. In this case, the processor unit determines a classification of healthy enamel responsive to the characteristic value being positive and determines a classification of unhealthy enamel responsive to the characteristic value being negative.

In some embodiments, computing the characteristic value comprises computing an estimate of a gradient of a slope of the reflection spectrum of the sampled surface between the respective wavelengths of the two measurements. For example, this may be based on computing a difference between the at least two reflection intensity measurement values already mentioned above and dividing by a difference in the wavelengths to which each measurement corresponds. In some embodiments, a series of (more than two) reflection intensity measurements may be obtained and wherein the gradient is computed from this series of measurements. There are known methods for computing a gradient value from a series of sample measurements.

In some embodiments, the at least two measurements include a first reflection intensity measurement within a wavelength sub-band of 550-600 nm, and a second intensity measurement within a wavelength sub-band of between 600-650 nm. This would result in a slope gradient values for example for the spectrum at a location centered around 600 nm. As will be demonstrated later, this is an optimal spectrum point at which the probe the gradient since it can be reliably expected to be negative for healthy enamel and non-negative for unhealthy enamel.

In some embodiments, computing the characteristic value comprises computing a ratio of the at least two reflection intensity measurements, and wherein a first of the at least two reflection intensity measurements is within a wavelength sub-band corresponding to green light, and a second of the at least two reflection intensity measurements is within a wavelength sub-band corresponding to red light. Thus a Green to Red reflectance intensity ratio is measured. As will be demonstrated later, this ratio can be reliably expected to be less than one for unhealthy enamel and more than one for healthy enamel.

In some embodiments, the light generator comprises one or more LEDs.

In some embodiments, the light detector comprises a camera.

In some embodiments, the light detector comprises one or more photodiodes.

In some embodiments, the light detector comprises at least one photodiode array.

In some embodiments, the output includes a data output or signal output.

In some embodiments, the output includes a data output, and wherein the device further includes a wireless communication module for communicating the data output to a secondary computing device.

In some embodiments, the output includes a user-perceptible output, such as a visual output or an acoustic output, generated through control of a user-output element.

In some embodiments, the device is an oral care device and further comprises an oral care apparatus adapted to perform an oral care function.

In some embodiments, the device is a toothbrush.

In some embodiments, the device is a brushing mouthpiece device.

In some embodiments, the device comprises an arrangement of cleaning elements for brushing teeth during use.

In some embodiments, the device is an oral irrigator. In some embodiments, the device is a powered flossing device, such as an air flossing device or liquid flossing device.

Another aspect of the invention is an optical analysis method. The method comprises control of a multi-frequency optical measurement apparatus comprising a light generator and a light detector, the light generator for irradiating a tooth surface with light during use, and the light detector for detecting a reflection of the light from the tooth surface during use. The light generator is operable to selectively generate a light output within each of a plurality of different wavelength bands, and/or the light detector is operable to differentially detect light at each of a plurality of wavelength bands. The method comprises:

controlling the optical measurement apparatus to acquire a spectroscopic measurement set comprising at least two reflection intensity measurements at two different and non-overlapping wavelength sub-bands, each sub-band within the range 550 and 650 nm;

computing a characteristic value from the at least two reflection intensity measurements, wherein the characteristic value is proportional to either a difference between the at least two reflection intensity measurements, or a ratio of the at least two reflection intensity measurements, whereby the characteristic value provides a direct or indirect indicator of a sign of a slope of a reflection spectrum of the sampled surface between the respective wavelengths of the at least two measurements;

determining a classification of healthy enamel vs unhealthy enamel based on the characteristic value; and generating an output indicative of the classification.

In some embodiments, the method further comprises a step of positioning the multi-frequency optical measurement apparatus within the mouth of a user such that the light generator and light detector are in optical communication with a tooth surface.

Any of the optional features described above in relation to the dental analysis device aspect of the invention can be applied also to this method aspect, to provide embodiments of the method aspect of the invention.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1 shows a block diagram of components of an oral analysis device in accordance with one or more embodiments of the invention;

FIG. 2 outlines steps of a method in accordance with one or more embodiments;

DETAILED DESCRIPTION OF THE EMBODIMENTS

Figure 3:
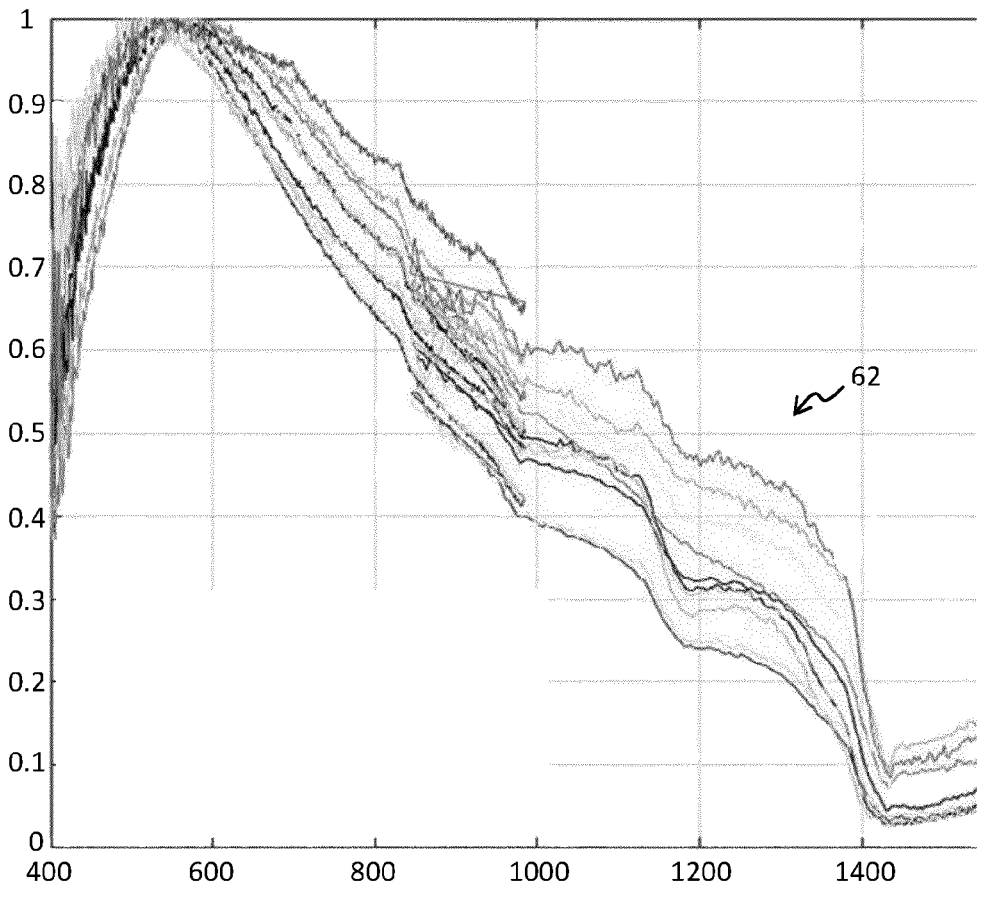
FIG. 3 shows an optical reflection spectrum obtained through experiment for a sample set of ten different tooth surfaces, all having healthy enamel (without caries)

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a device and method for providing a classification of tooth surface materials using measured reflectance values for light within a particular optical band which has been found by the inventors to be a particularly reliable predictor of presence or absence or oral caries. In particular, at least two optical reflectance measurements may obtained within an optical wavelength band of 550 nm to 650 nm, and wherein a characteristic value proportional to a difference or ratio of those measurements is computed. This effectively provides an indication, direct or indirect, of a sign of a slope of a reflectance spectrum within that band, and this has been identified through experiment as a reliable differentiator of healthy vs unhealthy enamel.

Thus, the inventive concept is based on a form of spectral analysis system. In general, such a system is designed to irradiate a surface with light having a certain intensity-wavelength relation and determine if changes of the intensity-wavelength relation are found in reflected light received back from the spectral analysis system. By intensity-wavelength relationship is simply meant a particular wavelength-intensity spectrum or composition of the light.

Embodiments may in particular rely on detection of diffuse light (diffuse reflectance spectroscopy). In this way, the embodiments of this invention may be differentiated from systems which rely on detecting fluorescence or which rely on use of coherent light. Non-coherent light may be generated and used (i.e. detected) in accordance with embodiments of the present invention.

Embodiments of the present invention propose to detect at least one characteristic of oral features by irradiating the oral features with light, and changes in the intensity-wavelength relation for the light may be taken as a measure of the characteristic.

FIG. 1 outlines in block diagram form components of an example device according to one or more embodiments. The device features will be recited in summary, before being explained further in the form of example embodiments.

The device comprises a multi-frequency optical measurement apparatus 14 which in turn comprises a light generator 16 and a light detector 18. As schematically illustrated, the light generator is 16 is for irradiating (during operation) a tooth surface 20 with light. The light generator is sometimes referred to in the art as a light engine, and may comprise a light supply unit for supplying light to be conveyed to a subject's oral cavity. The light detector is for detecting a reflection of the said same light from the tooth surface 20 during operation.

The light generator may include one or more light sources, e.g. LEDs. The light generator may include one or more optical processing components such as a luminescent converter and/or a light guide.

In order to perform the analysis, the light generator 16 may be configured operable to selectively generate a light output within each of a plurality of different wavelength bands, and/or the light detector 18 may be configured operable to differentially detect light at each of a plurality of wavelength bands.

There is further provided a processor unit 30 adapted to perform a processing method in relation to data 24 acquired by the optical measurement apparatus 14, and steps of this method will be described below. Although FIG. 1 shows the processor separated from the optical measurement apparatus 14, the two may be integrated in a single unit, for example held by a housing of single device. However, the processor unit could even be separate from the optical measurement apparatus 14, for example with the two communicatively linked.

The processor unit 30 is adapted to control the optical measurement apparatus to acquire a spectroscopic measurement set 24 comprising at least two reflection intensity measurements at two different and non-overlapping wavelength sub-bands, each sub-band within the range 550 and 650 nm The processor unit 30 is further adapted to compute a characteristic value from the at least two reflection intensity measurements, wherein the characteristic value is proportional to either a difference between the at least two reflection intensity measurements, or a ratio of the at least two reflection intensity measurements. In this way, the characteristic value can be understood as providing a direct or indirect indicator of a sign of a slope of a reflection spectrum of the sampled surface between the respective wavelengths of the at least two measurements. This will be explained with greater clarity with reference to figures later.

The processor unit 30 is further adapted to determine a classification 34 of healthy enamel vs unhealthy enamel based on the characteristic value.

The processor unit 30 is further adapted to generate an output from the processor unit indicative of the classification 34.

As was noted previously, the same inventive concept can also be embodied in the form of a method rather than an apparatus. To show this more explicitly, FIG. 2 outlines steps of method which is in accordance with one or more embodiments of the same inventive concept. The steps of this method will be outlined in summary form, and details will become more apparent through the remainder of this disclosure.

The method 40 comprises control of a multi-frequency optical measurement apparatus 14, such as that already described, comprising a light generator 16 and a light detector 18, the light generator for irradiating a tooth surface 20 with light during use, and the light detector 18 for detecting a reflection of the light from the tooth surface during use. As already described, the light generator may be operable to selectively generate a light output within each of a plurality of different wavelength bands, and/or the light detector 18 may be operable to differentially detect light at each of a plurality of wavelength bands.

The method 40 comprises at least the following steps:

receiving 42 from an optical measurement 14 apparatus a spectroscopic measurement set 24 comprising at least two reflection intensity measurements at two different and non-overlapping wavelength sub-bands, each sub-band within the range 550 and 650 nm;

computing 44 a characteristic value from the at least two reflection intensity measurements, wherein the characteristic value is proportional to either a difference between the at least two reflection intensity measurements, or a ratio of the at least two reflection intensity measurements, whereby the characteristic value provides a direct or indirect indicator of a sign of a slope of a reflection spectrum of the sampled surface between the respective wavelengths of the at least two measurements;

determining 46 a classification 34 of healthy enamel vs unhealthy enamel based on the characteristic value; and generating 48 an output indicative of the classification.

The method may be partially or wholly computer implemented. The method may be performed by a processing unit, such as the processing unit 30 already described.

In some embodiments, the method may further comprise a step of positioning the multi-frequency optical measurement apparatus 14 within the mouth of a user such that the light generator and light detector are in optical communication with a tooth surface 20. In this case, this step of the method would for example be performed by a human operator (or also conceivably a robot operator). In the former case, this step of the method would not be computer implemented. However, in the latter case, the step could be computer implemented by issuing control instructions to such a robot.

The invention can also be embodied in a computer program product comprising code means configured, when run on a processor or computer, to cause the processor or computer to perform a method in accordance with any example or embodiment outlined in this disclosure, or in accordance with any claim of this patent application.

Embodiments of the invention also relate to an oral examination device configured to be at least partially positioned in a subject's oral cavity for examination purposes, the oral examination device comprising a light engine as mentioned, and further relate to an oral examination system comprising such an oral examination device.

Embodiments of the invention also relate to an examination system capable of examining tissue types and communicating the examination results to a person.

The light source may comprise at least one LED. In case the light source comprises a plurality of LEDs, the LEDs may be positioned in the device in any configuration as desired. A plurality of LEDs may be provided for example as one or more arrays of LEDs.

The light detector is adapted to measure an intensity of light reflected by a tooth surface at two or more wavelengths, as mentioned above.

The light detector may comprise one or more photodiodes for this purpose.

The light detector may additionally or alternatively comprise a camera or camera chip for this purpose.

From the above, it can be appreciated that the inventive concept can be implemented using simple, readily available and low cost light generation and detection components, and this is aided, as will become clear, from the method of data analysis which relies on relative values of the two or more spectral intensity measurements, as opposed to absolute values.

The output 34 can include for example a data output carrying digital information representative of the classification, and/or or signal output.

The output may additionally or alternatively include a user-perceptible output, such as a visual output or an acoustic output, generated through control of a user-output element. The user output element may be a sensory output element.

The device may advantageously further include a wireless communication module for communicating the data or signal output to a secondary computing device.

The secondary computing device may be an external device or system which is separate from the oral examination device. This secondary computing device may include means for generating a user-perceptible output indicative of the information communicated to it, i.e. the classification 34.

By way of example, this secondary computing device may be a mobile computing device, for example a smartphone or tablet computer.

It is noted that embodiments of the invention can advantageously be used for both humans and animals, and the use of the term "subject" may be understood as encompassing non-human animals as well as humans.

Having now described in summary features of a device and method embodying the inventive concept, the details of the data processing and analysis will now be explained in greater depth.

As has already been explained, in embodiments, light at a number of different wavelengths is measured, to infer the presence of tooth material that is affected by caries. Affected tissue shows different optical reflection compared to healthy tissue. In addition, enamel and dentine show different optical properties. In general, caries is first visible in the enamel.

Figure 4:
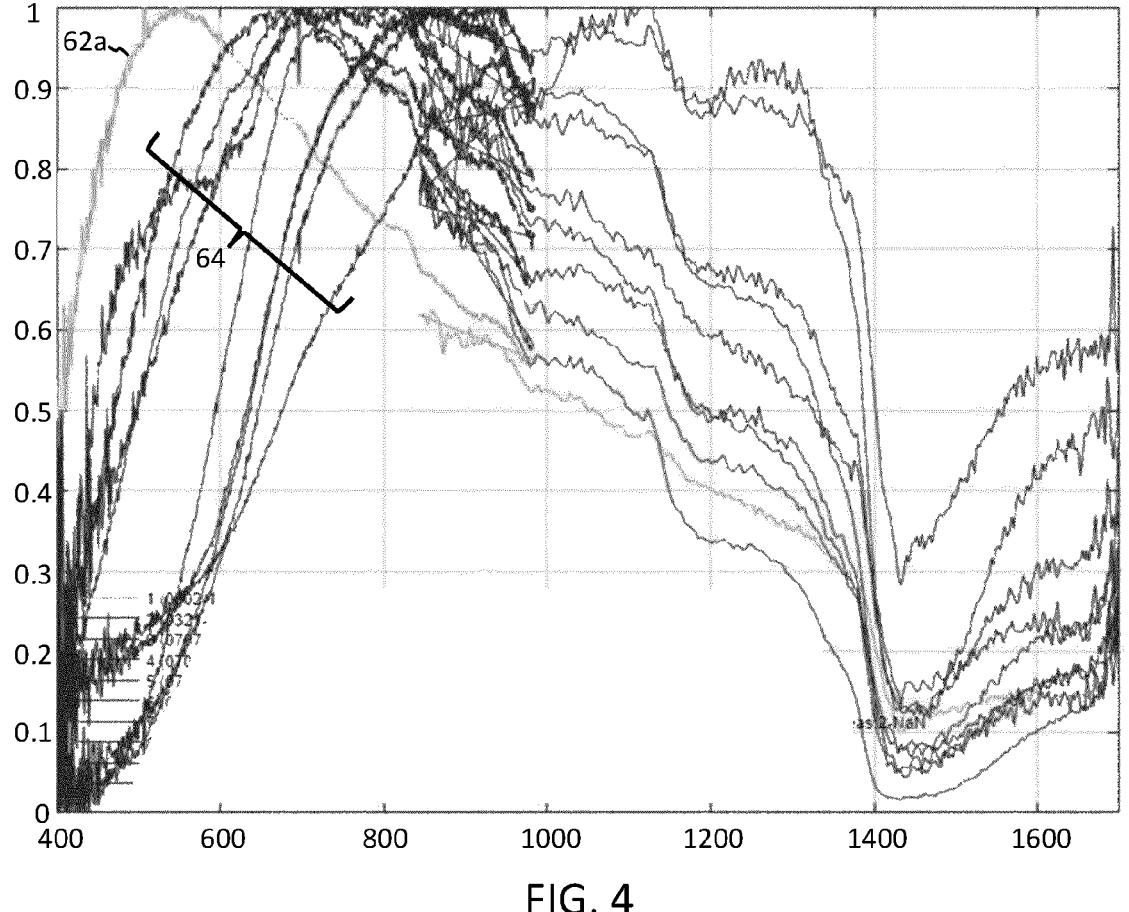
FIG. 4 shows optical reflection spectrum obtained through experiment for a sample set of ten different tooth surfaces, which includes a single spectrum for a tooth with healthy enamel, and nine spectra obtained for different respective tooth surfaces having unhealthy enamel (with caries, or with enamel at an early onset stage of caries).

To illustrate, reference is now made to FIG. 3 and FIG. 4.

FIG. 3 shows optical reflection spectra 62 obtained through experiment for a sample set of ten different tooth surfaces, all having healthy enamel (without caries). As can be seen, all of the spectra follow a very similar curve shape and trajectory. All of the spectra peak at approximately the same wavelength, namely approximately 550 nm Most importantly for the purposes of the present invention, it will be recognized that within the sub-band of 550-650 nm, the slope of the spectra curves are all negative, with the peak having occurred at approximately 550 nm.

FIG. 4 demonstrates experimental data for the comparator case of unhealthy enamel. For case of comparison, one of the example spectra 62a from the experiment represented by FIG. 3 is shown on the same set of axes in FIG. 4. FIG. 4 further shows a set of nine reflection spectra 64 obtained in experiment from nine different tooth surfaces, each comprising unhealthy enamel which is affected by caries. As can be seen, the peak in the case of unhealthy enamel in fact can vary, and this is reflective of the fact that caries admits of different degrees of severity, and can present with different particular characteristics in the effect on the material of the tooth. However, it will be observed that one very reliable characteristic of all of the spectra is that between the range 550 nm and 650 nm, the slope of the reflection spectrum is positive.

From this data represented in summary form in FIG. 3 and FIG. 4, it can be concluded that a spectroscopic measurement set which directly or indirectly indicates a negative sign slope of a reflectance spectrum at any point or subsection within the wavelength band 550 nm to 650 nm, or across the whole band, can be taken as indicative of healthy enamel, not affected by caries.

From this observation, multiple particular methods are possible for exploiting the identified distinguishing characteristic of the reflection spectra for the purpose of deriving a discriminatory detection of presence of diseased enamel and non-diseased enamel.

One way is to derive a measure of an (approximate) value of the slope at a point or sub-section of the relevant band 550 nm-650 nm, for example a point in the middle, at or around 600 nm. This could be done with, at minimum, two reflection intensity measurements, but also with more if practical and if desired. Another way is to take a difference of the reflection intensity value at two wavelengths within the band. Another way is to take a ratio of the reflection intensity value at two wavelengths within the band.

Taking these in reverse order, in the case of the ratio, here the characteristic value derived by the processor unit 30 from the at least two reflection intensity measurements is proportional to a ratio of the reflection intensity measurement of the lower of the at least two measured wavelengths to the intensity measurement of the higher of the at least two measured wavelengths. The processor unit 30 in this case determines a classification of healthy enamel responsive to the characteristic value being greater than or equal to 1 and determines a classification of unhealthy enamel responsive to the characteristic value being less than 1.

In the second of the above-outlined options (the difference case), here the characteristic value derived by the processor unit 30 from the at least two reflection intensity measurements is proportional to a value of the intensity measurement for the higher of the at least two measured wavelengths subtracted from the intensity measurement for the lower of the at least two measured wavelengths. The processor unit 30 in this case determines a classification of healthy enamel responsive to the characteristic value being positive and determines a classification of unhealthy enamel responsive to the characteristic value being negative.

In the first of the above-mentioned cases, the computing of the characteristic value by the processing unit 30 comprises computing an estimate of a gradient of a slope of the reflection spectrum of the sampled surface between the respective wavelengths of the two measurements. For example this could be based on computing a difference between the at least two reflection intensity measurement values and dividing by a difference in the wavelengths to which each measurement corresponds.

In any of the above options, the at least two reflection intensity measurements acquired using the optical measurement apparatus may include a first reflection intensity measurement within a wavelength sub-band of 550-600 nm, and a second intensity measurement within a wavelength sub-band of between 600-650 nm. This obtains for example a slope value for the spectrum at a location centered around 600 nm.

Indeed, as a more general principle, an advantageous embodiment comprises determining an estimate of a gradient of a slope of the reflection spectrum of the sampled surface across a subsection of the band 550-650 nm which is centered at 600 nm. Stated another way, an advantageous embodiment comprises determining an estimate of a gradient of a slope of the reflection spectrum of the sampled surface at or around the wavelength 600 nm.

The slope at 600 nm could for example be measured by using a multi-spectral light generator, comprising for instance two or more light sources generating light in the spectral range 550-600 nm and 600-650 nm respectively, and measuring reflection intensity obtained for each sub-band. In this case, a detector may be provided which has only a single detection band, i.e. is not spectrally discriminating. The single detection band could be for example approximately in the red region. It could be the band 550-650 nm. It could be a wider band than this. It could be configured to detect any visible light. However, use of a spectrally discriminating light detector in this case is also not ruled out and would be an option.

The light sources having the different spectral outputs may be operated sequentially for example, whereby the detected reflection does not need to be spectrally separated into spectral components; no spectral discrimination needs to be performed at the detection side.

This may require a one-time relative calibration factor for the different frequency light sources in the light generator, the calibration factor defining the relative light output intensity of the different frequency light sources in the light generator. In this way, when the single detector detects the intensity for each light source, any baseline difference in emission intensity (represented by the calibration factor) can be discounted when computing the characteristic value, e.g. by adjusting one or both of the measured intensity values, or adjusting the overall characteristic value.

Alternatively, where a multi-frequency discriminating detector is used, the sensitivity ratio of different detection bands of such a detector can be determined as a calibration factor, for example a one-time relative calibration factor of the green and red sensitive pixels of a camera.

It will of course be immediately recognized by the skilled reader that instead of generating the two light outputs sequentially in time, both could be generated simultaneously, and a spectrally discriminating detector used which is able to provide separate intensity measurements for the two spectral sub-bands.

It will also be recognized that instead of using two different light sources in the light generator with different spectral output characteristics, a single light source could be used which has a broad-band output which spans at least a portion of the range 550-650 nm and, wherein this is used in combination with a multi-spectral detector which is able to discriminatorily detect intensity within two or more different non-overlapping sub-ranges within said at least portion of the overall range.

It will also be immediately recognized that the above principles can be expanded for measurement of more than two data points (i.e. more than two wavelengths).

In some examples, more than two spectral intensity measurements could be obtained, wherein the additional measurements beyond two may all be within said same range of 550-650 nm, or some or all may be outside of said range 550-650 nm. By way of example, reflection intensity measurements could be acquired at each of 550 nm, 600 nm and 700 nm. This could be achieved by way of example by using at three light sources, emitting at 550 nm, 600 nm and 700 nm respectively. Such a configuration is suitable to measure the intensity values in the spectral region 550 nm-700 nm. Reflection maxima above 650 nm are always indicative of affected enamel.

Another possibility which has not yet been mentioned is to compute the characteristic value as a ratio of the at least two reflection intensity measurements, and wherein a first of the at least two reflection intensity measurements is within a wavelength sub-band corresponding to green light, and a second of the at least two reflection intensity measurements is within a wavelength sub-band corresponding to red light. This may be referred to for shorthand and the 'green to red ratio', or G/R intensity ratio. This in fact represents a sub-species of the more general example group already described of taking a ratio of two reflection intensity measurements, since both green and red cover regions within the range 550 nm-650 nm. Thus, in this case, the processor unit may determine a classification of healthy enamel responsive to the G/R ratio being greater than or equal to one, and may determine a classification of unhealthy enamel responsive to the G/R ratio being less than one.

By way of two illustrative examples, from the experimental data, the following criteria can be derived to distinguish healthy enamel (H) from enamel with caries (C)

11

TABLE 1

| Status enamel | G/R intensity ratio | Approximate slope at 600 nm (dI/dλ) (I/nm) |
|---|---|---|
| H | ≥1 | −0.001 |
| C | <1 | 0.0025 |

Of course, for the slope at 600 nm, a more general criterion, still consistent with that stated in the table is that if the slope is less than zero, then the enamel may be classified as healthy and is the slope is greater than zero, then the enamel may be classified as unhealthy (enamel with caries).

In some embodiments, the characteristic value may be monitored over time to detect changes in enamel status. In particular, the ratio, the difference or the slope values may be recorded in a dataset associated with the subject along with a time-stamp, and then historical values can be monitored and trended. If the ratio, difference or slope is moving further toward a classification of unhealthy enamel, this could be communicated to the patient to prompt them to change eating or cleaning habits; and if the ratio, difference or slope is moving further into the healthy range, then this could be communicated to the patient as a confirmation to continue their current cleaning or eating habits.

It is of advantage for example for the device to comprise storage capacity and software, such that trends can be computed from recorded historical data. Alternatively, the historical data may be stored on an external or remote data store, for example a memory module of a mobile computing device with which the analysis device is communicatively linked, or a cloud-based datastore.

In some embodiments, measurements and classification may be performed for multiple teeth in the mouth, and the result for each one recorded in the said dataset for the patient along with an identifier of the tooth to which each classification corresponds.

A caries risk score may in some examples be estimated, based on caries progression (size of the caries spot as well as the growth of the spot). In some examples, federated learning may be used whereby the accuracy of the risk score can be improved over time using brushing data from many users and by coupling this data to examination data from dentists and dental treatments.

In some embodiments, the optical analysis device may further comprise a position sensor for sensing a positioning of at least the optical measurement apparatus within the mouth as each spectroscopic measurement set is being acquired. In this way the oral position associated with each measurement set and corresponding classification can be automatically detected and recorded.

As mentioned above, in some embodiments, detection results may be communicated to a secondary computing device, such as a mobile computing device, such as a smartphone, tablet or the like, such that a person such as a dentist or other dental professional may be informed about the results. Such communication can take place at a long range such as through the Internet, or at a significantly shorter range.

The oral analysis device may comprise a battery for providing the power for driving the light generator, detector and processor. According to another possibility, the oral examination device may be connectable to a mains power supply.

In some embodiments, the oral analysis device may be oral care device which further comprises an oral care apparatus adapted to perform an oral care function. By way of example, the device may be a toothbrush or brushing mouthpiece comprising an arrangement of cleaning elements for brushing teeth during use. The oral analysis device may be included for example in the brush head of the toothbrush, but may alternatively be included in the handle of the toothbrush, for example. It may also be incorporated in a dental drill or an air-floss device for example.

In many cases, in the normal course of inspection of a subject's oral cavity is by a person such as a dental professional, a light source is used to irradiate the oral cavity with visible light. In accordance with some embodiments, the light generator may be used for the dual purpose of illuminating the oral cavity for providing visibility for a dental professional. The light may be therefore be visible light having a function in ensuring that the oral cavity or at least a portion thereof is brightly lit so that the person may have a clear view on the teeth, the gums and/or other oral features to be inspected. Additionally the light may have a function in the operation of the optical measurement apparatus.

Embodiments of the invention described above employ a processor unit. The processor unit may in general comprise a single processor or a plurality of processors. It may be located in a single containing device, structure or unit, or it may be distributed between a plurality of different devices, structures or units. Reference therefore to the processor unit being adapted or configured to perform a particular step or task may correspond to that step or task being performed by any one or more of a plurality of processing components, either alone or in combination. The skilled person will understand how such a distributed processor unit can be implemented. The processor unit may include a communication module or input/output for receiving data and outputting data to further components.

The one or more processors of the processor unit can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A dental analysis device, comprising:
a multi-frequency optical measurement apparatus comprising a light generator and a light detector, the light generator for irradiating a tooth surface with light during use, and the light detector for detecting diffuse reflection of the light from the tooth surface during use, wherein the light generator is operable to selectively generate a non-coherent light output within each of a plurality of different wavelength bands, and/or the light detector is operable to differentially detect light at each of a plurality of wavelength bands; and
a processor unit adapted to:
control the optical measurement apparatus to acquire a spectroscopic measurement set comprising at least two non-fluorescent diffuse reflection intensity measurements at two different and non-overlapping wavelength sub-bands, each sub-band within the range of 550 to 650 nm;
compute a characteristic value from the at least two diffuse reflection intensity measurements, wherein the characteristic value is proportional to either a difference between the at least two reflection intensity measurements, or a ratio of the at least two reflection intensity measurements, whereby the characteristic value provides a direct or indirect indicator of a sign of a slope of a reflection spectrum of the sampled surface between the respective wavelengths of the at least two measurements;
determining a classification of healthy enamel vs unhealthy enamel based on the characteristic value; and
generating an output from the processor unit indicative of the classification.

2. The device of claim 1, wherein the characteristic value is proportional to a ratio of the diffuse reflection intensity measurement of the lower of the at least two measured wavelengths to the intensity measurement of the higher of the at least two measured wavelengths, and wherein the processor unit determines a classification of healthy enamel responsive to the characteristic value being greater than or equal to 1 and determines a classification of unhealthy enamel responsive to the characteristic value being less than or equal to 1.

3. The device of claim 1, wherein the characteristic value is proportional to a value of the intensity measurement for the higher of the at least two measured wavelengths subtracted from the intensity measurement for the lower of the at least two measured wavelengths, and wherein the processor unit determines a classification of healthy enamel responsive to the characteristic value being positive and determines a classification of unhealthy enamel responsive to the characteristic value being negative.

4. The device of claim 3, wherein computing the characteristic value comprises computing an estimate of a gradient of a slope of the diffuse reflection spectrum of the sampled surface between the respective wavelengths of the two measurements, based on computing a difference between the at least two diffuse reflection intensity measurement values and dividing by a difference in the wavelengths to which each measurement corresponds.

5. The device of claim 1, wherein the at least two measurements include a first diffuse reflection intensity measurement within a wavelength sub-band of 550-600 nm, and a second diffuse reflection intensity measurement within a wavelength sub-band of between 600-650 nm.

6. The device of claim 1, wherein computing the characteristic value comprises computing a ratio of the at least two reflection intensity measurements, and wherein a first of the at least two reflection intensity measurements is within a wavelength sub-band corresponding to green light, and a second of the at least two reflection intensity measurements is within a wavelength sub-band corresponding to red light.

7. The device of claim 1, wherein the light generator comprises one or more LEDs.

8. The device of claim 1, wherein the light detector comprises a camera.

9. The device of claim 1, wherein the output includes a data output or signal output.

10. The device of claim 9, wherein the output includes a data output, and wherein the device further includes a wireless communication module for communicating the data output to a secondary computing device.

11. The device of claim 1, wherein the output includes a user-perceptible output, such as a visual output or an acoustic output, generated through control of a user-output element.

12. The device of claim 1, wherein the device is an oral care device and further comprises an oral care apparatus adapted to perform an oral care function.

13. The device of claim 12, wherein the device is a toothbrush or brushing mouthpiece comprising an arrangement of cleaning elements for brushing teeth during use.

14. An optical analysis method,
wherein the method comprises control of a multi-frequency optical measurement apparatus comprising a light generator and a light detector, the light generator for irradiating a tooth surface with light during use, and the light detector for detecting a reflection of the light from the tooth surface during use,
wherein the light generator is operable to selectively generate a light output within each of a plurality of different wavelength bands, and/or the light detector is operable to differentially detect light at each of a plurality of wavelength bands;
the method comprising:
controlling the optical measurement apparatus to acquire a non-fluorescent diffuse reflection intensity measurements diffuse reflection spectroscopic measurement set comprising at least two diffuse reflection intensity measurements at two different and non-overlapping wavelength sub-bands, each sub-band within the range 550 and 650 nm;
computing a characteristic value from the at least two diffuse reflection intensity measurements, wherein the characteristic value is proportional to either a difference between the at least two diffuse reflection intensity measurements, or a ratio of the at least two diffuse reflection intensity measurements, whereby the characteristic value provides a direct or indirect indicator of a sign of a slope of a reflection spectrum of the sampled surface between the respective wavelengths of the at least two measurements;

determining a classification of healthy enamel vs unhealthy enamel based on the characteristic value; and generating an output indicative of the classification.

15. The method of claim 14, further comprising a step of positioning the multi-frequency optical measurement apparatus within the mouth of a user such that the light generator and light detector are in optical communication with a tooth surface.

* * * * *